United States Patent [19]

Carbonell et al.

[11] Patent Number: 5,167,925
[45] Date of Patent: * Dec. 1, 1992

[54] PRECIPITATION OF MULTIVALENT ANTILIGANDS WITH AFFINITY SURFACTANTS

[75] Inventors: Ruben G. Carbonell; Roberto Guzman; Peter K. Kilpatrick, all of Raleigh, N.C.

[73] Assignee: North Carolina State University

[*] Notice: The portion of the term of this patent subsequent to May 12, 1992 has been disclaimed.

[21] Appl. No.: 861,471

[22] Filed: Apr. 1, 1992

Related U.S. Application Data

[63] Continuation of Ser. No. 204,424, Jun. 8, 1988, Pat. No. 5,112,770.

[51] Int. Cl.$^5$ ............... G01N 33/539; G01N 33/536
[52] U.S. Cl. ...................... 422/61; 436/536; 436/538; 436/539; 436/808
[58] Field of Search ............. 436/536, 538, 539, 808; 422/61

[56] References Cited

U.S. PATENT DOCUMENTS

| | | |
|---|---|---|
| 4,195,074 | 3/1980 | Safford, Jr. ............... 424/12 |
| 4,469,796 | 9/1984 | Axen et al. ............... 436/828 |
| 4,522,803 | 6/1985 | Lenk et al. ............... 424/1.1 |
| 4,529,712 | 7/1985 | Jou et al. ............... 436/519 |
| 4,563,445 | 1/1986 | Feizi et al. ............... 514/25 |
| 4,564,599 | 1/1986 | Janoff et al. ............... 436/507 |
| 4,598,051 | 7/1986 | Papahadjopoulos et al. ...... 436/512 |
| 4,605,630 | 8/1986 | Kung et al. ............... 436/511 |
| 4,617,262 | 10/1986 | Maxim et al. ............... 436/828 |
| 4,624,921 | 11/1986 | Larrick et al. ............... 435/172.2 |
| 4,636,479 | 1/1987 | Martin et al. ............... 436/533 |
| 4,657,849 | 4/1987 | Kallenuius et al. . |
| 4,668,638 | 5/1987 | Janoff et al. ............... 436/506 |
| 4,675,392 | 6/1987 | Dahmen et al. ............... 536/17.6 |
| 4,741,831 | 4/1988 | Grinstead et al. ............... 210/641 |
| 4,743,560 | 5/1988 | Campbell et al. ............... 436/501 |
| 4,751,219 | 6/1988 | Kempen et al. ............... 424/450 |
| 4,780,409 | 10/1988 | Monji et al. ............... 435/7 |
| 4,885,172 | 12/1989 | Bally et al. ............... 474/450 |
| 4,913,902 | 1/1990 | Kilpatrick et al. ............... 414/88 |
| 5,112,770 | 5/1992 | Carbonell et al. ............... 436/501 |

OTHER PUBLICATIONS

Bangs, L., *Uniform Latex Particles*, 51–58, (Published by: Seragen Diagnostics, Inc., 800-248-4007).

*Primary Examiner*—Jill A. Johnston
*Attorney, Agent, or Firm*—Bell, Seltzer, Park & Gibon

[57] ABSTRACT

Surfactants bound to a ligand and dissolved in a single phase aqueous solution form a precipitate when a multivalent antiligand is added to the solution. This invention can be used in an affinity precipitation test procedure (and kit) for detecting the presence or absence of a multivalent antiligand in a sample suspected of containing the multivalent antiligand, in an affinity precipitation inhibition test procedure (and kit) for detecting the presence or absence of a target ligand in a sample suspected of containing the target ligand, and in a process for separating a multivalent antiligand from a crude material containing the multivalent antiligand.

16 Claims, No Drawings

PRECIPITATION OF MULTIVALENT ANTILIGANDS WITH AFFINITY SURFACTANTS

This application is a continuation of pending prior U.S. application Ser. No. 07/204,424, filed Jun. 8, 1988, now issued as U.S. Pat. No. 5,112,770.

FIELD OF THE INVENTION

This invention relates to diagnostic tests generally, and particularly relates to diagnostic tests in which multivalent antiligands are precipitated from a solution with affinity surfactants. Broadly, this invention also relates to a method of separating multivalent antiligands from a crude solution.

BACKGROUND OF THE INVENTION

Particle agglutination procedures are widely used for immunodiagnostic tests. These procedures employ particles coated with ligands, usually antigens, which bind to multivalent antiligands in a solution. Numerous different types of particles, including glass beads and latex particles, are used in these types of tests, the latex particle tests being generally illustrative of this technology.

Both direct and indirect latex agglutination tests are known, with direct tests used to detect antibodies in solution and indirect tests used to detect antigens in solution. In a typical direct latex agglutination test, latex particles coated with antigens are combined with a solution suspected of containing an antibody. If an antibody is present, it cross-links, or agglutinates, the latex particles, agglutination signaling the presence of the antibody. In a typical indirect latex agglutination test, both latex particles coated with antigen and a known quantity of an antibody which binds the antigen are combined together with a solution suspected of containing a target antigen which also binds with the antibody. If the target antigen is present, agglutination of the latex particles by the antibody is inhibited, with inhibition of agglutination signaling the presence of the antibody. See L. Bangs, *Uniform Latex Particles,* 51–58 (published by Seragen Diagnostics, Inc., P.O. Box 1210, Indianapolis, Ind. 46202). Through these two applications of the particle agglutination phenomenon, a broad variety of diagnostic tests are available.

The high cost of uniform latex particles and the difficulty of binding antigens to these particles have led to the development of numerous alternative agglutination tests. One approach is to use liposomes (or even cells) as the particle to be agglutinated. See, e.g., U.S. Pat. No. 4,668,638 to Janoff et al.; U.S. Pat. No. 4,636,479 to Martin et al.; U.S. Pat. No. 4,598,051 to Papahadjopoulos et al.; U.S. Pat. No. 4,564,599 to Janoff et al.; and U.S. Pat. No. 4,529,712 to Jou et al. These procedures require that the antigen be bound to some type of particle. Another approach is to combine a lipid antigen with an emulsion of lipid droplets, the lipid droplets serving as the particles to be agglutinated. See, e.g., U.S. Pat. No. 4,605,630 to Kung et al. at column 1, line 65 to column 2, line 16. This requires the use of a double phase solution (an emulsion) as a test reagent. Still another approach was described by Larsson P. O. and Mosbach, K., *FEBS Letters* 98, 333 (1979). In their scheme, the bifunctional nucleotide $N_2N_2'$-adipodihydrazido-bis-($N^6$-carbonylmethyl-NAD), or Bis-NAD, was synthesized and added to a solution of the tetrameric enzyme lactate dehydrogenase (LDH), for which NAD is a strong ligand. The simultaneous binding of the bifunctional ligand to two different LDH molecules leads to aggregation and network formation of an enzyme-ligand complex. A disadvantage of this approach is that it is limited to the specific bifunctional ligand synthetic scheme disclosed.

Because of the importance of immunoassay procedures as diagnostic tests in the health care field and the limitations inherent in the procedures described above, there is a continuing need for simple and inexpensive agglutination tests. The present invention provides such a test.

DESCRIPTION OF THE INVENTION

The present invention is based on our finding that surfactants, when bound to a ligand and dissolved in a single phase aqueous solution, form a precipitate when a multivalent antiligand is added to the solution.

A first aspect of the present invention is an affinity precipitation test procedure for detecting the presence or absence of a multivalent antiligand in a sample suspected of containing the multivalent antiligand. This procedure comprises, first, providing a single phase aqueous solution having therein dissolved an affinity surfactant, the affinity surfactant comprising a surfactant having a ligand bound thereto, which ligand binds to the antiligand. Next, the sample is combined with the single phase aqueous solution. Finally, the presence of a precipitate comprised of an affinity surfactant—multivalent antiligand aggregate in the solution is determined, the presence of the precipitate indicating the presence of the multivalent antiligand in the solution.

A second aspect of the present invention is an affinity precipitation inhibition test procedure for detecting the presence or absence of a target ligand in a sample suspected of containing the target ligand. The procedure involves providing a multivalent antiligand which binds to the target ligand, and providing a single phase aqueous solution having therein dissolved an affinity surfactant. The affinity surfactant comprises a surfactant having a ligand bound thereto, the ligand bound to the surfactant being selected to compete with the target ligand for binding to the multivalent antiligand. In the process, the sample, the multivalent antiligand, and the single phase aqueous solution are combined, and the degree of formation of a precipitate comprised of an affinity surfactant—multivalent antiligand aggregate in the solution determined. The precipitate is formed when the target ligand is absent from the sample and the precipitate is inhibited from forming when the target ligand is present in the sample.

A third aspect of the present invention is an affinity precipitation test kit for detecting the presence or absence of a multivalent antiligand in a sample suspected of containing the multivalent antiligand. The test kit comprises a single phase aqueous solution having therein dissolved an affinity surfactant. The affinity surfactant comprises a surfactant having a ligand bound thereto, which ligand binds to the antiligand, the affinity surfactant being present in an amount effective to produce a precipitate when a sample containing the multivalent antiligand is combined with the single phase aqueous solution. The precipitate to be formed comprises an affinity surfactant—multivalent antiligand aggregate.

A fourth aspect of the present invention is an affinity precipitation inhibition test kit for detecting the presence or absence of a target ligand in a sample suspected of containing the target ligand. The test kit comprises a multivalent antiligand which binds to the target ligand, and a single phase aqueous solution having therein dissolve an affinity surfactant. The affinity surfactant comprises a surfactant having a ligand bound thereto, the ligand bound to the surfactant selected to compete with the target ligand for binding to the multivalent antiligand. The affinity surfactant and the multivalent antiligand are each present in an amount effective to produce a precipitate when combined with one another and a sample which does not contain the target ligand. In addition, the affinity surfactant and the multivalent antiligand are each present in an amount effective to produce a measurably smaller quantity of precipitate when combined with one another and a sample which does contain the target ligand.

A fifth aspect of the present invention is a process for separating a multivalent antiligand from a crude material containing the multivalent antiligand (i.e., a material containing the multivalent antiligand and other compounds in combination). The process comprises, first, providing a single phase aqueous solution having therein dissolved an affinity surfactant. The affinity surfactant comprises a surfactant having a ligand bound thereto, which ligand binds to the antiligand. The crude material is then combined with the single phase aqueous solution to thereby form a precipitate comprised of an affinity surfactant—multivalent antiligand aggregate in the solution. The precipitate is then separated from the solution, and the multivalent antiligand recovered from the precipitate.

Affinity surfactants useful in the present invention have the general formula A-B-L, where A is a hydrophobic (or nonpolar) functional group, B is a hydrophilic (or polar) functional group, and L is a ligand which specifically binds to a target molecule. The A and B groups together comprise the surfactant to which the ligand "L" is bound. Preferably, A, B, and L are bound together covalently.

One group of surfactants useful for practicing the present invention is the amphipathic lipids, that is, lipids which possess a polar head (the "B" group), and a nonpolar tail (the "A" group). Specific examples of suitable lipids useful in the present invention are phospholipids, which include, but are not limited to, the natural lecithins or phosphatidylcholines (e.g., egg lecithin or soybean lecithin) and synthetic lecithins, such as saturated synthetic lecithins (e.g., dimyristoylphosphatidylcholine, dipalmitoylphosphatidylcholine and distearoylphosphatidylcholine) and unsaturated synthetic lecithins (e.g., dioleoylphosphatidylcholine and dilinoleoylphosphatidylcholine). Other useful phospholipids include, but are not limited to, phosphatidylethanolamine, lysolecithin, lysophosphatidylethanolamine, phosphatidylserine, phosphatidylinositol, sphingomyelin, cardiolipin, phosphatidic acid, ceramides and cerebrosides. A preferred phospholipid is phosphatidylethanolamine. Preferably, affinity surfactants formed from amphipathic lipids and which are not directly soluble in an aqueous solution may be used in the present invention by adding a solubilizing surfactant to the solution, which solubilizing surfactant is effective to dissolve the affinity surfactant in the aqueous solution. Any suitable surfactant may be used as the solubilizing surfactant, with those surfactants described in the following paragraph (when not bound to a ligand) being illustrative of suitable solubilizing surfactants.

Another group of surfactants useful in practicing the present invention comprises those in which the polar "B" group is a hydrophilic spacer arm of the type conventionally used in affinity chromatography and having a substitution site at each end. See generally Lowe, C. and Dean, P., *Affinity Chromatography*, 218–220 (1974). Preferably, however, surfactants of this type are those in which the polar group is a polyalkoxy group having at least two alkoxy groups selected from the class consisting of ethoxy and isopropoxy. Broadly speaking, the polyalkoxy group will have not more than 50 alkoxy groups. Preferably, however, the polyalkoxy group will have from 5 to 30 alkoxy groups therein. A ligand (the "L" group) can be substituted for the hydroxyl group at one end of the polyalkoxy group and a hydrophobic functional group (the "A" group) substituted for the hydroxyl group at the other end of the polyalkoxy group by known procedures. The hydrophobic functional group may be a benzyl group or a linear or branched alkyl group having from 2 to 50 carbon atoms and any degree of unsaturation. Preferably, the hydrophobic group is a linear alkyl group having from 8 to 50 carbon atoms. Exemplary alkyl groups are octyl, decyl, dodecyl, tetradecyl, hexadecyl, octadecyl, and eicosyl. Use of surfactants of this type is believed an improvement to the present invention, in that they do not require the presence of a solubilizing surfactant. Specific examples of surfactants of this type are "Sandopan TA36," which may be obtained from the Sandoz Chemical Company, and octaethylene glycol n-hexadecyl ether ($C_{16}E_8$) which may be obtained from Nikkol Chemicals Company (Japan). In all of these surfactants, minor substitutions to polyalkoxy groups which do not substantially affect the polarity of the polyalkoxy groups produce equivalent surfactants for purposes of this invention. Fluorinated polyalkoxy groups are exemplary of such equivalent compounds.

The terms "ligand" and "antiligand," as used herein, designate the opposite members of a high affinity binding air. Illustrative examples of such high affinity binding pairs include antigen-antibody and biotin-avidin. Multivalent antiligands are antiligands which have two or more ligand binding sites spatially arranged to promote bridging between two or more different affinity surfactants. These terms have the same meaning herein as conventionally used in the art. See, e.g., U.S. Pat. No. 4,636,479 to Martin et al., at column 1, line 37–66. (Applicants specifically intend that the disclosure of this and all other patent references cited herein be incorporated herein by reference.)

Preferably, solutions to be tested and crude materials to be purified by the present invention are substantially free of hydrophobic contaminants. The term "substantially free" does not mean completely free; it only means that the amount of hydrophobic contaminants is not so great that they completely disrupt aggregate formation. Other information and guidelines useful for practicing the present invention is set forth in the immunoassay literature, reflected in part by the literature cited herein.

The following examples are provided to illustrate a few specific embodiments of the present invention, and are not to be taken as restrictive thereof. In conducting the experiments described in the examples, Dimyristoylphosphatidylethanolamine (DMPE), biotinyl-N-hydroxysuccinimide ester (BNHS), triethylamine, myoglobin, bovine serum albumin (BSA), lysozyme, guanidinium chloride, dimethylaminocinnamaldehyde, and molybdenum blue reagent were all obtained from Sigma Chemicals and used without further purification as received. Avidin was obtained from Vector Laboratories with a quoted activity of 14 units per milligram. All solvents were from Fisher Scientific. Water was passed through a Barnstead Nanopure system.

EXAMPLE 1

Preparation of Biotinylated Phospholipid

Biotin was coupled to dimyristoyl phosphatidylethanolamine (DMPE) according to the procedure of Bayer, E. A. et al., *Biochim. Biophys. Acta* 550, 464 (1979). 48 micromoles (umol) of DMPE was dissolved in a 1 milliliter (ml) solution of chloroform/methanol (volume ratio 2:1) containing 60 umol of biotinyl-N-hydroxysuccinimide ester (BNHS). 10 microliters (ul) of triethylamine was added to act as a proton-accepting catalyst and the mixture was allowed to react at room temperature for thirty minutes. The biotinylated DMPE (DMPE-B) was separated from unreacted BNHS by preparative thin-layer chromatography on 1 millimeter (mm) thick silica gel plates, using chloroform/methanol/water (volume ratio 80:25:2) as the developing solvent system. The biotinylated phospholipid was identified by both a biotin-specific spray reagent (dimethylaminocinnamaldehyde, 0.2% in acidified ethanol), see McCormick, D. B. and Roth, J. A., *Meth. Enzymol.* 18, 383 (1970), and a phosphate-specific spray (molybdenum blue reagent), see Dittmer, J. and Lester, R. C., *J. Lipid Res.* 5, 126 (1964). The product was scraped off the plate and extracted with chloroform/methanol (volume ratio 2:1). The solvent was evaporated at 40° C. in a rotary evaporator and the dry product was weighed to determine the yield. Typically, 75% of the theoretical yield was obtained. The DMPE-biotin was stored under nitrogen at $-4°$ C.

EXAMPLE 2

Determination of Avidin Activity

The ultraviolet spectrum of avidin in aqueous buffer solution is observed to shift to the red (hyperchroic effect) when biotin binds to one of the four avidin active sites, see Green, N. M., *Biochem. J.* 89, 585 (1963). The maximum shift in the spectrum occurs at 233 nanometers (nm) and thus a plot of absorbance at 233 nm of avidin solution with differing amounts of added biotin versus amount of biotin added yields a titration plateau at the stoichiometric endpoint (four biotins per avidin molecule for completely active avidin). Absorbance measurements were made on a Shimadzu model UV-265 double-beam recording spectrophotometer. Three ml of a standard avidin solution in 0.2 Molar (M) ammonium carbonate, typically 0.068 milligrams per millimeter (mg/ml) or $10^{-6}$M, were placed in the sample cuvette and this was zeroed against 3 ml of buffer solution. Aliquots of concentrated biotin in buffer solution were then added to both cuvettes and the increase in absorbance was determined for each aliquot until further addition of biotin resulted in no change in absorbance. The resulting titration plateau was used to calculate the number of biotin molecules binding to each avidin molecule. The stoichiometric ratio of 4:1 is obtained, indicating our standard avidin is essentially 100% active.

EXAMPLE 3

Dissolution of Biotinylated Phospholipid in Nonionic Surfactant Solution

Solutions of the nonionic surfactant octaethylene glycol mono-n-dodecyl ether ($C_{12}E_8$) at a concentration of $10^{-3}$M in 0.2M ammonium carbonate buffer at pH 8.9 were used to solubilize DMPE-B to obtain solutions of $5\times10^{-5}$M and $1.25\times10^{-4}$M of the modified phospholipid. The phospholipid was suspended in 100 ml of the $C_{12}E_8$ solutions and the mixture was vigorously stirred with heating to a uniform temperature of 60°-70° Celcius (C.) for about 45 minutes, whereupon a single phase aqueous solution of DMPE-Biotin $C_{12}E_8$ (DMPE-B-$C_{12}E_8$ solution) was obtained.

EXAMPLE 4

Titration of Avidin with Solubilized DMPE-B

In an effort to understand the mechanism and kinetics of binding affinity-modified phospholipid to avidin, hyperchroic and turbidimetric titrations of avidin solutions were performed by adding small sequential aliquots of DMPE-B-$C_{12}E_8$ solution to avidin and by adding large single aliquots to a protein solution. In one experiment, 3.0 ml of an $8.82\times10^{-7}$M avidin solution in standard buffer (0.2M ammonium carbonate at pH 8.9) was placed in the sample cell of the spectrophotometer and 3.0 ml of standard buffer in the reference cell, with the absorbance reading at 233 nm zeroed. Small aliquots (40 ul) of concentrated DMPE-B-$C_{12}E_8$ solution ($5.0\times10^{-5}$ and $10^{-3}$M, respectively) were then added to both reference and sample cell and the absorbance change monitored until a steady-state value was obtained. The maximum value of the absorbance reached, 0.682 at ca. 240 ul of solution added, far exceeds the absorbance value corresponding to the hyperchroic shift in a simple avidin-biotin titration, ca. 0.063 for this concentration of avidin, and was in fact a combination of a hyperchroic shift and turbidity due to the appearance of large aggregates in solution, the bulk of the absorbance due to turbidity. This maximum absorbance corresponds to a Molar ratio of DMPE-B to avidin of 4.5 to 1, which slightly exceeds the stoichiometric ratio of 4:1 for complete binding of DMPE-B to avidin.

For these values of absorbance, the avidin solutions are visibly turbid, indicating the presence of large super-molecular aggregates. Our interpretation of this observation is that upon binding of DMPE-B molecules to two different avidin molecules, hydrophobic interactions between the exposed surfactant tail groups lead to oligomer formation. Because avidin possesses four binding sites per molecule, each protein can interact simultaneously with tail groups on four other avidin molecules. The result is the formation of a three-dimensional network of avidin-DMPE-B complex which ultimately phase separates as a precipitate and can be sedimented or centrifuged.

In the titration experiment just described, the concentration of nonionic surfactant ($C_{12}E_8$) at the absorbance maximum is about $8.0\times10^{-5}$M, just slightly below its critical micelle concentration (CMC) of about $10^{-4}$M. As additional aliquots of DMPE-B-$C_{12}E_8$ solution are added to the avidin solution, the absorbance values begin to decrease, suggesting sedimentation of the avidin-DMPE-B complexes. This is confirmed by the low value of the absorbance (ca. 0.08) observed for the solution when it was allowed to stand overnight with no agitation.

The kinetics of aggregate formation were assessed by adding one large aliquot of concentrated DMPE-B-$C_{12}E_8$ solution to a standard avidin solution ($8.82\times10^{-7}$M in buffer) such that the ratio of DMPE-B to avidin in the solution was 3.8:1. Within a few seconds after addition, the change in absorbance of the avidin solution reached the hyperchroic titration endpoint of about 0.055. The absorbance remained at this value for more than ten minutes, whereupon apparent aggregation began to occur and the absorbance began to steadily increase over a 20-30 minute period and asymptotically approach a steady value of 0.666. This final absorbance is in good agreement with the value obtained by sequential addition.

EXAMPLE 5

Precipitation and Recovery of Avidin from Solution

To test the efficacy of precipitating avidin from solution as a means of separating this protein from other protein impurities, a series of experiments were performed with pure proteins. Standard solutions of avidin ($10^{-6}$M in 0.2M ammonium carbonate aqueous buffer) were adjusted to pH 8.9, which is the pH of strongest avidin-biotin binding. A standard avidin solution was mixed with concentrated DMPE-B-$C_{12}E_8$ solution so that the final concentration was $10^{-6}$M avidin, $4\times10^{-6}$ DMPE, and $7.5\times10^{-5}$M $C_{12}E_8$. To this standard protein solution, a sufficient aliquot of concentrated DMPE-B-$C_{12}E_8$ solution was added to yield a final concentration of $4\times10^{-6}$M DMPE-B and $7.5\times10^{-5}$M $C_{12}E_8$, i.e., a 4:1 stoichiometric ratio of DMPE-B to avidin. This was found to be the optimal ratio for precipitation of avidin, as will be discussed below. After two hours, the absorbance of the solution had reached a steady value of about 0.68 and the mixture was centrifuged at 5000 rpm for twenty minutes. The supernatants were analyzed by ultraviolet absorbance at 281 nm to determine residual protein concentration in solution. The solid pellet was typically resuspended in $10^{-3}$M $C_{12}E_8$ solution and analyzed by UV absorbance. The solution was found to contain ca. 70% of the original avidin. In instances where the amount of active avidin recoverable was determined, the avidin was dissociated from the DMPE-B by addition of 6M guanidinium chloride at pH 1.5. the resulting avidin subunits were then reconstituted by a 15-fold dilution with standard ammonium carbonate buffer followed by ultrafiltration through a YM-5 membrane (Amicon). The avidin activity was then measured by the hyperchroic titration procedure described in Example 2 above.

EXAMPLE 6

Precipitation and Recovery of Avidin from a Mixed Avidin and Myoglobin Solution

A protein mixture containing $10^{-6}$M avidin and $10^{-6}$M myoglobin in standard buffer was prepared for affinity precipitation to test the specificity of the method. Myoglobin was selected as a test impurity because it possesses an absorbance maximum at 410 nm, which does not overlap the uv-visible spectrum of avidin; thus, the concentrations of the two proteins could be analyzed by simple absorbance. Upon addition of concentrated surfactant solution, so that the final concentrations were $4\times10^{-6}$M DMPE-B and $7.5\times10^{-5}$M $C_{12}E_8$, the onset of turbidity was observed. After four hours, the sample was centrifuged at 5000 rpm for twenty-five minutes and the solid separated from the supernatant. Analysis of the supernatant shows that 93% of the myoglobin remains in solution while the resolubilized solid in $C_{12}E_8$ solution shows no absorbance at 410 nm. From the absorbance at 281 nm of the resuspended pellet, it was estimated that 68% of the avidin was recovered by precipitation. A second aliquot of DMPE-B was added to the supernatant (to give a DMPE-B concentration of $10^{-6}$M) and the solution once again became turbid with time. After four hours, the solution was centrifuged, the solid separated from supernatant and resolubilized in $C_{12}E_8$ solution. Analysis of the resolubilized solid indicated that an additional 18% of the avidin was precipitated with no concommitant precipitation of myoglobin. Thus, the two precipitation steps combined yeilded 86% of the original avidin, with no apparent co-precipitation of myoglobin.

EXAMPLE 7

Precipitation and Recovery of Avidin from a Mixed Avidin and BSA Solution and from a Mixed Avidin, BSA and Lysozyme Solution Experiments similar to those described in Examples 5 and 6 were performed on solutions of avidin and BSA (both $10^{-6}$M) and avidin, BSA, and lysozyme (all $10^{-6}$M). In the avidin/BSA system, a total of 77% of the original avidin was recovered in resolubilized precipitate, while in the avidin/BSA/lysozyme system, 87% of the original avidin was recovered in resolubilized precipitate. As a control, solutions of myoglobin in buffer ($10^{-6}$M), BSA in buffer ($10^{-6}$M), and BSA plus lysozyme in buffer (both $10^{-6}$M) were mixed with concentrated surfactant solution to obtain mixture concentration of $4\times10^{-6}$M DMPE-B and $7.5\times10^{-5}$M $C_{12}E_8$. In each case, no turbidity developed in the solution and no precipitate was obtained upon prolonged centrifugation. Thus, it appears that precipitation is completely specific to the protein to which the affinity surfactant binds specifically.

EXAMPLE 8

Precipitation of Avidin from Partially Purified Egg Whites

In order to test the applicability of the described precipitation procedure for purifying avidin from a naturally occurring crude biological mixture, a preliminary ion exchange purification of the avidin source hen egg whites was performed. This was necessary as there are numerous hydrophobic contaminants, such as membrane lipids and ovomucoids, in egg whites which tend to interfere with the hydrophobic interactions in the aggregation process. Initially, 40 grams of carboxymethylcellulose (CMC) from Pharmacia (CM-Sephadex) was hydrated with deionized water at 80° C. using a ratio of 10 grams of CMC per liter of water. The hydrated gel was washed several times by decantation to remove fines and then packed into a 100 cm×5 cm glass column. The column was washed according to Melamed and Green, see Melamed, M. D., and Green, N. M., *Biochem. J.* 89, 591 (1963), with a half liter of 0.5 NaCL, 0.5N NaOH aqueous solution, followed by distilled water (4 liters), 1 mM EDTA solution (2 liters), and finally again with distilled water (4 liters). After washing, the gel was removed from the column and dried on a fritted glass funnel with gentle suction. The washing with water helps to remove small amounts of soluble CMC, which can complex avidin, see Green, N. M., *Biochem. J.* 89, 585 (1963), and the washing with EDTA helps to remove metal ions which can denature avidin. See Fraenkel-Conrat, H. et al., *Arch. Biochem. Biophys.* 39, 80 (1952).

Egg white from 15 eggs (ca. 0.5 liter) was gently homogenized with an equal volume of cold deionized water. A small amount of precipitate was removed by centrifuging at 4000 rpm for 30 minutes. The pretreated dried CMC (10 grams) was stirred into the homogenized egg white supernatant with a resulting suspension pH of 7.1. At this pH, only proteins in the egg whites with isoelectric points exceeding 7.0 bind to the CMC. After settling the CMC, the supernatant was siphoned off and a second fraction of the dried pretreated gel (10 grams) was added to the solution. Again the gel was settled and the supernatant removed, whereupon a third fraction of dried gel (10 grams) was added to the solution. The three sedimented gel fractions were combined and washed with five liters of 50 mM ammonium acetate buffer at pH 7.0. The gel was transferred to a fritted glass funnel and washed again with one liter of 50 mM ammonium acetate. These washings were intended to remove residual fines which could plug the column during elution of the proteins. The gel was washed a final time with 2 liters of 50 mM ammonium acetate, but now at pH 8.86, still below the pH of the desired avidin. The gel was then suspended in 3 liters of 50 mM ammonium acetate buffer at pH 9.0. The suspension was degassed and poured into the glass column, at the bottom of which the last fraction of the dry pretreated CMC was packed under hydrostatic pressure. The packed column was then washed with 1.5 liters of 50 mM ammonium acetate at pH 9.0 at a flowrate of 5.0 ml/min. The column was next washed with 0.8 liters of 0.3 wt % ammonium carbonate, pH 9.0, at the end of which the eluent absorbance at 281 nm was 0.04. The adsorbed proteins were then eluted with a stepwise gradient of ammonium carbonate, pH 9.0 from 0.4% to 1.2% in increments of 0.1% and 500 ml of eluting buffer. A uniform flowrate of 5.0 ml/min was maintained; at the end of the elution, the gel had compacted 25 cm, or about 30%. Assuming a void fraction of 0.4, the total elution time through the column was estimated to be 2.5 hours corresponding to about 750 ml of eluting buffer. Avidin, along with other globulin proteins, eluted primarily in the peak corresponding to an eluting buffer concentration of from 0.5 to 0.8% ammonium carbonate. The eluting solutions were collected in 500 ml fractions and were concentrated by ultrafiltration by tenfold using a YM10 Amicon flat membrane.

The avidin content of the fractions eluted from the ion exchange column were determined by reverse phase HPLC analysis using an Alltech octyl-bonded silica column, a Perkin Elmer Series 410 quaternary solvent delivery system with environmental chamber, a Perkin Elmer model UV-95 ultraviolet-visible detector, and Rheodyne injection valve. A standard gradient of 10 minutes for protein elution was applied from 90% water, 10% acetonitrile, 0.1% TFA to 100% acetonitrile, 0.1% TFA. After determination of avidin content of a solution fraction, an aliquot of DMPE-B-$C_{12}E_8$ solution was added to precipitate avidin such that the molar ratio of DMPE-B to avidin was slightly greater than the stoichiometric 4:1 ratio. To recover active avidin, the precipitated solid was redissolved with a $10^{-3}M$ $C_{12}E_8$ solution. Avidin was dissociated from DMPE-B by addition of 6M guanidinium chloride, and avidin subunits were renatured by diluting with 0.2M ammonium carbonate buffer and ultrafiltration through a YM5 membrane.

The final purity of the reconstituted avidin was assessed by its activity according to a hyperchroic titration, its ultraviolet spectrum, and an SDS-PAGE analysis. See generally Smith, B. J., SDS-Polyacrylamide Gel Electrophoresis of Proteins, in *Methods in Molecular Biology*, Vol. 1, Chap. 6 (J. M. Walker ed., 1984).

Following the ion exchange fractionation of egg white solution described above, fractions of eluted protein solution were mixed with DMPE-B-$C_{12}E_8$ solutions to effect affinity precipitation. The disappearance of free avidin from the solutions after aggregation and precipitation was characterized by reverse phase HPLC. The peak eluting at a retention time of 10.2 minutes was avidin, while the other smaller peaks were impurities in the solvent used for the gradient elution. A reverse phase chromatogram of a sample from the fraction eluting between 0.6 and 0.7% ammonium acetate in eluting buffer showed that the peak at retention time 10.27 minutes was avidin, with a large impurity protein peak at 11.24 minutes in addition to the solvent impurities seen in the standard avidin chromatogram. After affinity precipitation and centrifugation of this fraction, the chromatogram peak eluting at 10.3 minutes was reduced in area for equal volume injections of fraction and supernatant following precipitation by 91%, indicating virtually all of the avidin precipitated. This precipitate was resolubilized in 5 ml of $10^{-3}M$ $C_{12}E_8$ solution and analyzed by reverse phase HPLC. The peak at retention time 10.14 minutes corresponded to resolubilized avidin, while the other peaks are all artifacts or solvent impurities observed upon application of the gradient described above.

The recovered avidin precipitate was dissociated from DMPE-B and renatured according to the procedure described above. A standard biotin titration indicated that at least 80% of the reconstituted avidin was in active form.

The foregoing examples are illustrative of the present invention, and are not to be taken as restrictive thereof. The invention disclosed herein is defined by the following claims, with equivalents of the claims to be included therein.

We claim:

1. An affinity precipitation test kit for detecting the presence or absence of a multivalent antiligand in a sample suspected of containing said multivalent antiligand, said test kit comprising a single phase aqueous solution having therein dissolved an affinity surfactant, said affinity surfactant comprising a surfactant having a ligand bound thereto, which ligand binds to said multivalent antiligand, with said affinity surfactant being present in an amount effective to produce a precipitate when a sample containing said multivalent antiligand is combined with said single phase aqueous solution, said precipitate comprising an affinity surfactant—multivalent antiligand aggregate, said aggregate formed from repeating surfactant-to-surfactant hydrophobic interactions.

2. A test kit as claimed in claim 1, wherein said ligand is an antigen and said multivalent antiligand is an antibody.

3. A test kit as claimed in claim 1, wherein said ligand is biotin and said multivalent antiligand is avidin.

4. A test kit as claimed in claim 1, wherein said surfactant comprises an amphipathic lipid having a polar head group and a nonpolar tail group, and wherein said ligand is bound to said polar head group.

5. A test kit as claimed in claim 1, wherein said surfactant comprises a polar group bound to a nonpolar group, wherein said ligand is bound to said polar group, and wherein said polar group comprises a polyalkoxy group having at least two alkoxy groups.

6. A test kit as claimed in claim 5, wherein said alkoxy groups are selected from the class consisting of ethoxy and isopropoxy, and wherein said nonpolar group is selected from the class consisting of benzyl and linear and branched alkyl groups having from two to fifty carbon atoms and any degree of unsaturation.

7. An affinity precipitation inhibition test kit for detecting the presence or absence of a target ligand in a sample suspected of containing said target ligand, said test kit comprising a multivalent antiligand which binds to said target ligand and a single phase aqueous solution having therein dissolved an affinity surfactant, said affinity surfactant comprising a surfactant having a ligand bound thereto, said ligand bound to said surfactant selected to compete with said target ligand for binding to said multivalent antiligand, with said affinity surfactant and said multivalent antiligand each being present in an amount effective to produce a precipitate when combined with one another and a sample which does not contain said target ligand, and with said affinity surfactant and said multivalent antiligand each being present in an amount effective to produce a measurably smaller quantity of precipitate when combined with one another and a sample which does contain said target ligand.

8. A test kit as claimed in claim 7, wherein said ligand is an antigen and said multivalent antiligand is an antibody.

9. A test kit as claimed in claim 7, wherein said ligand is biotin and said multivalent antiligand is avidin.

10. A test kit as claimed in claim 7, wherein said surfactant comprises an amphipathic lipid having a polar head group and a nonpolar tail group, and wherein said ligand is bound to said polar head group.

11. A test kit as claimed in claim 10, wherein said single phase aqueous solution further comprises a solubilizing surfactant effective to dissolve said affinity surfactant in said single phase aqueous solution.

12. A test kit as claimed in claim 7, wherein said surfactant comprises a polar group bound to a nonpolar group, wherein said ligand is bound to said polar group, and wherein said polar group comprises a polyalkoxy group having at least two alkoxy groups.

13. A test kit as claimed in claim 12, wherein said alkoxy groups are selected from the class consisting of ethoxy and isopropoxy, and wherein said nonpolar group is selected from the class consisting of benzyl and linear and branched alkyl groups having from two to fifty carbon atoms and any degree of unsaturation.

14. An affinity precipitation test kit for detecting the presence or absence of a multivalent antiligand in a sample suspected of containing said multivalent antiligand, said test kit comprising a single phase aqueous solution having therein dissolved an affinity surfactant, said affinity surfactant comprising a surfactant having a ligand bound thereto, which ligand binds to said antiligand, with said affinity surfactant being present in an amount effective to produce a precipitate when a sample containing said multivalent antiligand is combined with said single phase aqueous solution, said precipitate comprising an affinity surfactant—multivalent antiligand aggregate;

and wherein said single phase aqueous solution further comprises a solubilizing surfactant effective to dissolve said affinity surfactant in said single phase aqueous solution.

15. A test kit as claimed in claim 14, wherein said ligand is an antigen and said multivalent antiligand is an antibody.

16. A test kit as claimed in claim 14, wherein said ligand is biotin and said multivalent antiligand is avidin.

* * * * *

UNITED STATES PATENT AND TRADEMARK OFFICE
CERTIFICATE OF CORRECTION

PATENT NO. : 5,167,925

DATED : December 1, 1992

INVENTOR(S) : Ruben G. Carbonell; Roberto Guzman; Peter K. Kilpatrick

It is certified that error appears in the above-identified patent and that said Letters Patent is hereby corrected as shown below:

On the title page: Notice: correct "May 12, 1992" to read -- May 12, 2009--.

Signed and Sealed this

Sixteenth Day of November, 1993

Attest:

BRUCE LEHMAN

Attesting Officer        Commissioner of Patents and Trademarks